United States Patent [19]

Schmidt, Jr.

[11] Plant 4,157

[45] Nov. 22, 1977

[54] MOUNTAIN ASH TREE

[76] Inventor: John Frank Schmidt, Jr., 19343 NE. Halsey St., Portland, Oreg. 97230

[21] Appl. No.: 754,521

[22] Filed: Dec. 27, 1976

[51] Int. Cl.[2] ..... A01H 5/12

[52] U.S. Cl. ..... Plt./51

[58] Field of Search ..... Plt./51

*Primary Examiner*—Robert E. Bagwill

*Attorney, Agent, or Firm*—Klarquist, Sparkman, Campbell, Leigh, Hall and Whinston

[57] ABSTRACT

A novel mountain ash characterized by its rapid growth rate, remarkably straight trunk, and large foliage which is dark green.

2 Drawing Figures

The present invention relates to a new and distinct variety of mountain ash tree of the species botanically known as *Sorbus tianshanica.*

My new variety originated from a process of repeated selections performed under my supervision and on cultivated property under my control at Boring, Oreg. More specifically, a number of years ago a large group of *Sorbus tianshanica* seedlings were grown from seeds which I have purchased. Thereafter, a small number of seedlings were selected from the large group on the basis of distinctive characteristics evidenced therein, primarily their more rapid growth rate.

Subsequently, a second large group of trees were obtained from these selected seedlings by budding. Seeds obtained from this second large group of trees, as a result of open pollination of them, were then planted to produce an additional sizable group of seedlings. A small number of seedlings were then selected from this sizable group mainly on the basis of their faster rate of growth and still another large group of trees were obtained from these selected seedlings by budding.

A small number of trees were then selected from this last large group, again primarily on the basis of their rapid growth rate, and were budded to produce still another sizable group of trees. As these trees grew, it became evident that three of them exhibited a new and improved combination of characteristics never previously exhibited in any *Sorbus tianshanica* tree of which I am aware. Although my records are not sufficient to identify which was the parent tree and the group of trees which included the parent were destroyed before the parent was identified, the identical characteristics, so far as observable, of these three trees has caused me to conclude that they are from a common parent tree. Close observations of these three trees and continued observations of progeny thereof, which possessed identical characteristics so far as observable, subsequently asexually propagated under my direction in Boring, Oreg. by budding has convinced me that my new tree represents a new and improved variety of *Sorbus tianshanica.* Furthermore, these observations have confirmed that my new variety is particularly evidenced by the following unique combination of characteristics which have proven firmly fixed, are outstanding therein, and which distinguish it from all other varieties of this species:

1. An extremely rapid, vigorous and upright habit of growth;

2. A remarkably straight trunk;

3. Extraordinarily large foliage with leaflets which are unusually dark green in color;

4. An exceptionally large proportion of the surface area of young petioles and newly formed branches is a reddish color; and

5. Remarkably late fall changes.

The accompanying photographs depict the color of the foliage of my new variety as nearly true as is reasonably possible to make the same in a color illustration of this character.

FIG. 1 is a color photograph of a tree of the present invention taken in mid-June 1976;

FIG. 2 is a color photograph of a leaf of the tree of my invention taken at the same time as the photograph of FIG. 1.

The primary distinguishing feature of my new tree over other trees of this species is its extremely rapid rate of growth. As a specific example, in the fall of 1976 measurements were made of the growth of approximately 100 trees of my new variety. These measurements revealed that, during their first growing season, the central stem of these trees grew an average of about 146 cm in length when measured from the place of budding to the understock. In contrast, similar measurements of a group of other *Sorbus tianshanica* trees growing in the same area disclosed that they grew an average of about 108 cm.

In the spring following their first growing season, *Sorbus tianshanica* trees form a flower at the tip of the central stem and the stem no longer grows taller. To increase the height of these trees, it is common practice to cut the flower from the central stem and tape up a lower branch, called a leader, so that it extends upwardly and becomes the growing stem for the tree. Eventually the new leader will also form a flower at its tip and cease growing. Consequently, the practice of taping up a new leader usually must be repeated one or more times, depending upon the height of the tree which is desired. Although these trees will be taller, their trunks will have a crook at each location where a leader is taped up. Since my variety grows faster than ordinary varieties, it will have a straight trunk. That is, the trunks of trees of my variety will have fewer crooks because the number of repetitions of the process of taping up a new leader required to produce a tree of a given height is reduced from the number required to produce an ordinary *Sorbus tianshanica* tree of similar height. In addition, to prevent a shrub-like appearance that otherwise might result, the lower branches of *Sorbus tianshanica* trees are often removed. In an ordinary tree of this species, the first crook (meaning the one nearest the ground) is commonly located in the limbed region of the trunk where it is highly visible. In contrast, the first crook of my variety is much less noticeable because it is located higher above ground where it is typically hidden to some extent by lower branches remaining on the tree.

As mentioned previously, the foliage of my tree is very large and contributes to its distinctive appearance. Moreover, due to its long petioles and large heavy leaflets, the leaves of my tree tend to bend downwardly more so than typical of the leaves of ordinary *Sorbus tianshanica* trees. This feature gives the leaves of my tree a highly ornamental weeping effect. In addition, when compared to known varieties, the leaflets of my tree are a darker green color and a greater proportion of the surface area of the young petioles and the new growth branches of my tree is a reddish color.

The leaves of my new variety changes from green to their autumn color and fall from the tree approximately 2 to 3 weeks later than similar changes in other *Sorbus tianshanica* trees.

Otherwise, my new variety is generally typical of the species.

The following is a detailed description of my new variety of *Sorbus tianshanica* tree, with color terminology in accordance with the "Royal Horticultural Society Color Chart" (hereinafter R.H.S.), published by the Royal Horticultural Society of London.

Parentage: A variety originating from a process of repeated selection.

Propagation: Holds to distinguishing characteristics through succeeding propagation by budding.

Locality were grown and observed: Boring, Oreg.

Tree: Upright, healthy; very vigorous; rapid growing; straight trunk.

Foliage:

*Leaves.*—Shape — pinnately compound. Size — Length (from the base of petiole to tip of leaflet at end of petiole) from about 31 cm to about 41 cm; Breadth (at the widest point from the tip of one leaflet to the tip of the laterally opposed leaflet) from about 14 cm to about 20 cm; Number of leaflets — Typically from 15 to 19 leaflets per leaf.

*Leaflets.*—Shape — lanceolate. Apex — acuminate. Base — acute. Margin — Serrate, entire near base. Size — Typically the largest leaflet of a leaf will be from about 7 cm to about 10 cm long and from about 2 cm to about 3 cm broad. Color — as described above and more specifically: The leaflets are a dark green color (similar to RHS 137–A) in contrast to the somewhat lighter green coloration (like RHS 137–B) of other known varieties.

Young petioles and new growth branches: A reddish coloration typical of the species (like RHS plate 184), but over a greater surface area than other known varieties of this species.

Fall changes: Occur approximately 2 to 3 weeks later than similar changes in ordinary *Sorbus tianshanica* trees.

I claim:

1. A new and distinct variety of mountain ash tree substantially as herein shown and described, characterized particularly as to novelty by a unique combination of its rapid rate of growth, a trunk which for a tree of a given height is straighter than the trunk of a tree of an ordinary variety of similar height, large foliage with dark green leaflets, a large proportion of the surface area of young petioles and newly formed branches is reddish color, and fall changes which occur approximately 2 to 3 weeks later than similar changes in ordinary varieties.

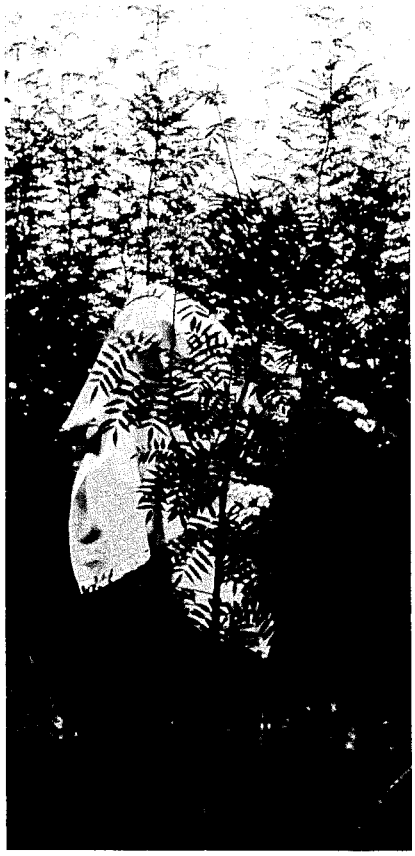
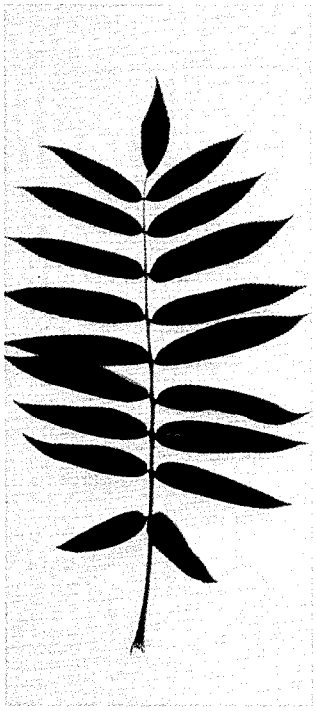

* * * * *